US012773407B2

(12) United States Patent
Huggett et al.

(10) Patent No.: US 12,773,407 B2
(45) Date of Patent: Oct. 27, 2026

(54) METHODS OF MANAGING COCAINE OR OTHER DRUG ADDICTIONS

(71) Applicants: Emory University, Atlanta, GA (US); Clemson University Research Foundation, Clemson, SC (US)

(72) Inventors: Spencer B. Huggett, Atlanta, GA (US); Rohan H. C. Palmer, Atlanta, GA (US); Robert Anholt, Greenwood, SC (US); Trudy MacKay, Greenwood, SC (US)

(73) Assignees: Emory University, Atlanta, GA (US); Clemson University Research Foundation, Clemson, SC (US)

( * ) Notice: Subject to any disclaimer, the term of this patent is extended or adjusted under 35 U.S.C. 154(b) by 464 days.

(21) Appl. No.: 18/023,797

(22) PCT Filed: Aug. 30, 2021

(86) PCT No.: PCT/US2021/048188
§ 371 (c)(1),
(2) Date: Feb. 28, 2023

(87) PCT Pub. No.: WO2022/047289
PCT Pub. Date: Mar. 3, 2022

(65) Prior Publication Data
US 2024/0024325 A1 Jan. 25, 2024

Related U.S. Application Data

(60) Provisional application No. 63/071,596, filed on Aug. 28, 2020.

(51) Int. Cl.
*A61K 31/519* (2006.01)
*A61K 31/5513* (2006.01)
(Continued)

(52) U.S. Cl.
CPC ........ *A61K 31/519* (2013.01); *A61K 31/5513* (2013.01); *A61K 45/06* (2013.01); *A61P 25/30* (2018.01)

(58) Field of Classification Search
CPC .... A61K 31/519; A61K 31/5513; A61P 25/30
(Continued)

(56) References Cited

U.S. PATENT DOCUMENTS

| | | | |
|---|---|---|---|
| 5,075,341 | A | 12/1991 | Mendelson |
| 7,514,444 | B2 | 4/2009 | Honigberg |

(Continued)

FOREIGN PATENT DOCUMENTS

| | | |
|---|---|---|
| WO | 2008039218 | 4/2008 |
| WO | 2015071432 | 5/2015 |
| WO | 2020150517 | 7/2020 |

OTHER PUBLICATIONS

Chiamulera C, Padovani L, Corsi M. Drug discovery for the treatment of substance use disorders: novel targets, repurposing, and the need for new paradigms. Current opinion in pharmacology. Aug. 1, 2017;35:120-4. (Year: 2017).*

(Continued)

*Primary Examiner* — Jeffrey S Lundgren
*Assistant Examiner* — Heather Dahlin
(74) *Attorney, Agent, or Firm* — Emory Patent Group

(57) ABSTRACT

This disclosure relates to using compounds disclosed herein to treat or prevent cocaine use disorder, cocaine toxicity, or other drug related disorders. In certain embodiments, this disclosure relates to methods of treating drug addiction or to help prevent relapse. In certain embodiments, this disclosure relates to methods of treating or preventing cocaine use disorder, cocaine toxicity, or other use disorders comprising administering an effective amount of a compound disclosed herein, such as ibrutinib, [(R)-1-(3-(4-amino-3-(4-phenoxy- (Continued)

phenyl)-1H-pyrazolo[3,4-d]pyrimidin-1-yl)piperidin-1-yl) prop-2-en-1-one], derivative, or salt thereof to a subject in need thereof. In certain embodiments, the compound is a Bruton's tyrosine kinase (BTK) inhibitor.

13 Claims, 4 Drawing Sheets

(51) Int. Cl.
*A61K 45/06* (2006.01)
*A61P 25/30* (2006.01)

(58) Field of Classification Search
USPC .......................................................... 514/262.1
See application file for complete search history.

(56) References Cited

U.S. PATENT DOCUMENTS

| | | | |
|---|---|---|---|
| 2005/0203098 | A1 | 9/2005 | Moussy |
| 2008/0108636 | A1 | 5/2008 | Honigberg |
| 2017/0342165 | A1 | 11/2017 | Norman |
| 2018/0185375 | A1 | 7/2018 | Detke |

OTHER PUBLICATIONS

Cameron F, Sanford M. Ibrutinib: first global approval. Drugs. Feb. 2014;74:263-71. (Year: 2014).*
Ferguson LB, Ozburn AR, Ponomarev I, Metten P, Reilly M, Crabbe JC, Harris RA, Mayfield RD. Genome-wide expression profiles drive discovery of novel compounds that reduce binge drinking in mice. Neuropsychopharmacology. May 2018;43(6):1257-66. (Year: 2018).*
O'Brien C. Addiction and dependence in DSM-V. Addiction. May 2011;106(5):866-7. (Year: 2011).*
Bannon et al. A Molecular Profile of Cocaine Abuse Includes the Differential Expression of Genes that Regulate Transcription, Chromatin, and Dopamine Cell Phenotype, Neuropsychopharmacology (2014) 39, 2191-2199.
Cunha-Oliveira et al. Cocaine as a Neurotoxin, R.M. Kostrzewa (ed.), Handbook of Neurotoxicity, 2014, pp. 277-297.
Ekpenyong-Akiba et al. Amelioration of age-related brain function decline by Bruton's tyrosine kinase inhibition, Aging Cell. 2020;19:e13079.
Ferguson et al. Genome-Wide Expression Profiles Drive Discovery of Novel Compounds that Reduce Binge Drinking in Mice, Neuropsychopharmacology (2018) 43, 1257-1266.
Huggett et al. Cocaine'omics: Genome-wide and transcriptome-wide analyses provide biological insight into cocaine use and dependence, Addiction Biology. 2020, 25:e12719.
Huggett et al. Ibrutinib as a Potential Therapeutic for Cocaine Use Disorder, medRxiv preprint doi: https://doi.org/10.1101/2021.02.05.21251228.
Ozbum et al. Effects of Pharmacologically Targeting Neuroimmune Pathways on Alcohol Drinking inMice Selectively Bred to Drink to Intoxication, Alcohol Clin Exp Res, vol. 44, No. 2, 2020: pp. 553-566.
Ribeiro et al. Gene Network Dysregulation in Dorsolateral Prefrontal Cortex Neurons of Humans with Cocaine Use Disorder, Sci Rep, 2017, 7(1):5412.
Subramanian et al. A Next Generation Connectivity Map: L1000 platform and the first 1,000,000 profiles, Cell. 2017, 171(6): 1437-1452.
Zhou et al. Substance-specific and shared transcription and epigenetic changes in the human hippocampus chronically exposed to cocaine and alcohol, Proc Natl Acad Sci U S A, 2011, 108(16):6626-31.

* cited by examiner

METHODS OF MANAGING COCAINE OR OTHER DRUG ADDICTIONS

CROSS-REFERENCE TO RELATED APPLICATIONS

This application is the National Stage of International Application No. PCT/US2021/048188 filed Aug. 30, 2021, which claims the benefit of U.S. Provisional Application No. 63/071,596 filed Aug. 28, 2020. The entirety of each of these applications is hereby incorporated by reference for all purposes.

STATEMENT REGARDING FEDERALLY SPONSORED RESEARCH OR DEVELOPMENT

This invention was made with government support under DA042103 and DA041613 awarded by the National Institutes of Health. The government has certain rights in this invention.

BACKGROUND

Cocaine is a highly addictive substance. Cocaine addicts often experience anxiety, depression, paranoia, and are at risk for heart attacks, strokes, overdose, intractable addiction, and post-abstinence relapse. Cocaine use disorder (CUD) is characterized by continued use despite adverse consequences. While behavioral treatments for cocaine use disorders (CUDs) exist, there are currently no approved medications. Thus, improved therapies are needed.

Huggett et al. report genome-wide and transcriptome-wide analyses provide biological insight into cocaine use and dependence. Addiction Biology, 2020, 25:e12719.

Subramanian et al. report L1000 platform Connectivity Map (CMap), whereby genes, drugs and disease states are connected by virtue of common gene-expression signatures. Cell, 2017, 171(6): 1437-1452.e17.

Ribeiro et al. report gene network dysregulation in dorsolateral prefrontal cortex neurons of humans with cocaine use disorder. Sci Rep, 2017, 7(1):5412.

Bannon et al. report a molecular profile of cocaine abuse includes the differential expression of genes. Neuropsychopharmacology, 2014, 39, 2191-2199.

Zhou et al. report substance-specific and shared transcription and epigenetic changes in the human hippocampus chronically exposed to cocaine and alcohol. PNAS, 2011, 108 (16) 6626-6631.

Ferguson et al. report genome-wide expression profiles drive discovery of compounds that reduce binge drinking in mice. Neuropsychopharmacology 2018; 43(6):1257-66.

References cited herein are not an admission of prior art.

SUMMARY

This disclosure relates to using compounds disclosed herein to treat or prevent cocaine use disorder, cocaine toxicity, or other drug related disorders. In certain embodiments, this disclosure relates to methods of treating drug addiction or to help prevent relapse. In certain embodiments, this disclosure relates to methods of treating or preventing cocaine use disorder, cocaine toxicity, or other use disorders comprising administering an effective amount of a compound disclosed herein such as ibrutinib, [(R)-1-(3-(4-amino-3-(4-phenoxyphenyl)-1H-pyrazolo[3,4-d]pyrimidin-1-yl)piperidin-1-yl)prop-2-en-1-one], derivative, or salt thereof to a subject in need thereof. In certain embodiments, the compound is a Bruton's tyrosine kinase (BTK) inhibitor.

In certain embodiments, the subject has admitted having or is diagnosed with an addiction to cocaine, methamphetamine, alcohol, tobacco, opioids, or other addictive drug, or diagnosed with, at risk of, or exhibiting symptoms of such a drug addiction. In certain embodiments, the subject is a human patient. In certain embodiments, the subject has accepted the terms of an inpatient or outpatient drug rehabilitation treatment plan.

In certain embodiments, a compound disclosed herein or a Bruton's tyrosine kinase (BTK) inhibitor such as ibrutinib is administered in combination with cocaine. In certain embodiments, the compound is administered in combination with methadone, buprenorphine, naltrexone, or other drugs to deter addiction in a medication-assisted treatment.

In certain embodiments, the subject has ceased to ingest cocaine or other addictive drug for more than 2 days, 3 days, 4 days, 5 days, 6 days, or 7 days. In certain embodiments, the subject has ceased to ingest cocaine or other addictive drug for more than 2 weeks or 3 weeks.

In certain embodiments, this disclosure relates to methods of preventing or treating a cocaine use disorder comprising administering an effective amount of a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof, to a subject in need thereof.

In certain embodiments, this disclosure relates to methods of treating or preventing a relapse of cocaine use comprising administering an effective amount of a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

In certain embodiments, this disclosure relates to methods of treating or preventing cocaine neurotoxicity comprising administering an effective amount of a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

In certain embodiments, this disclosure relates to methods of treating or preventing cocaine-induced seizures comprising administering an effective amount of a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

(male cocaine+ibrutinib), 66 (female control), 141 (female cocaine), 142 (female cocaine+Ibrutinib).

Figure 3A:
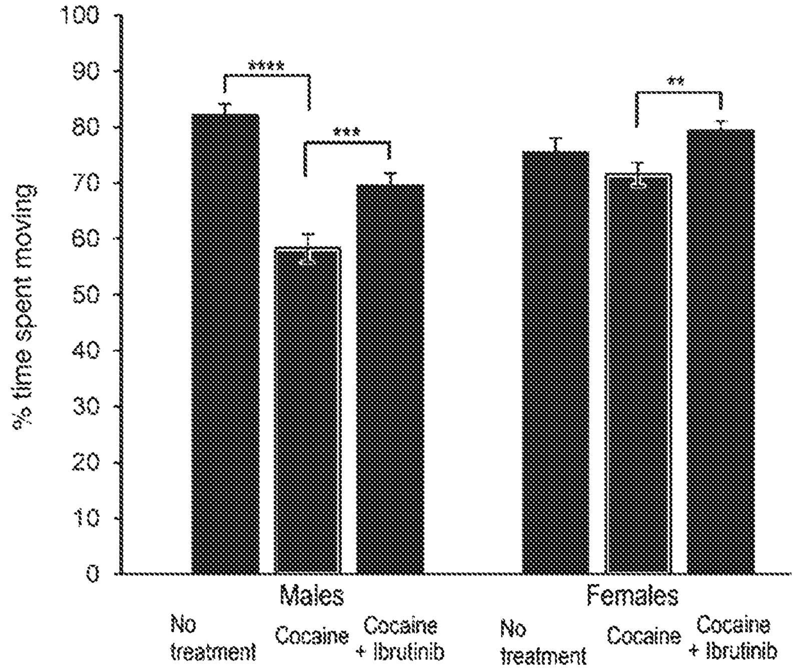
FIG. 3A-B shows data indicating ibrutinib mitigates cocaine-induced startle response and cocaine-induced seizures in *Drosophila melanogaster*. Sample sizes were as follows: (n=61 (male control), 140 (male cocaine), 132

FIG. 3A shows startle response data. The percent time out of 45 seconds that each fly spent moving following a 42 cm drop was measured. Male flies exposed to cocaine spent less time moving than flies exposed to untreated food ($p=2.13\times10^{12}$). Male and female flies exposed to cocaine and ibrutinib exhibited an increase in the percent of time spent moving compared to flies only exposed to cocaine. Error bars represent standard error.

Figure 3B:
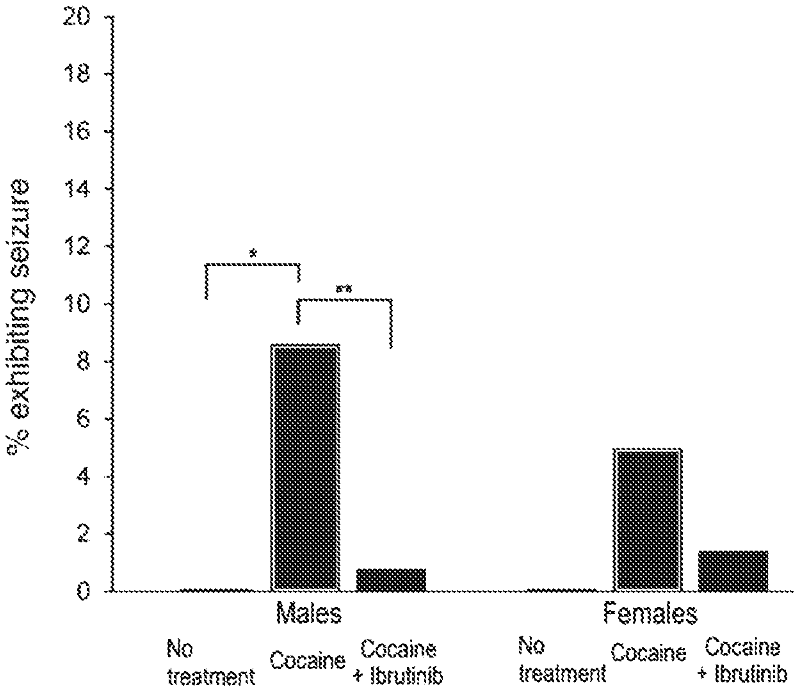

FIG. 3B shows data on seizure activity during the startle response. The number of flies that exhibited seizure activity during the startle assay was recorded. Male flies exposed to cocaine exhibited more seizure activity than flies exposed to untreated food.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps. "Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps composition components or method steps, etc., that do not materially affect the basic and novel characteristic(s) of the compositions or methods, compared to those of the corresponding compositions or methods disclosed herein.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals. In certain embodiments, the subject is a human.

As used herein, "cocaine used disorders" or "cocaine-related disorders" include cocaine dependence, addition, overdue and/or relapse, and any other disorder resulting in whole or in part from cocaine use. In addition to being a monotherapy, co-therapies are also contemplated. For example, when treating someone in rehabilitation to prevent relapse, a compound, e.g., ibrutinib or derivatives thereof as disclosed herein, can be optionally administered in combination with treatments for withdrawal symptoms (for example, administration of amantadine and propranolol). The compound can be used in conjunction with counseling and psychotherapy. In addition, the compound can also be used in combination with other agents that assist in the treatment of addiction to other drugs of abuse or medicaments.

As used herein, the term "combination with" when used to describe administration with an additional treatment means that the agent may be administered prior to, together with, or after the additional treatment, or a combination thereof.

An "effective amount" refers to an amount sufficient to elicit the desired biological response, i.e., treating the condition. As will be appreciated by those of ordinary skill in this art, the effective amount may vary depending on such factors as the desired biological endpoint, the pharmacokinetics of the compound, the condition being treated, the mode of administration, and the age and health of the subject. An effective amount encompasses therapeutic and prophylactic treatment.

Ibrutinib is a drug of the chemical formula (R)-1-(3-(4-amino-3-(4-phenoxyphenyl)-1H-pyrazolo[3,4-d]pyrimidin-1-yl)piperidin-1-yl)prop-2-en-1-one or salt thereof. In certain embodiments, it is contemplated that ibrutinib is formulated having the R enantiomer in enantiomeric excess of greater than 90, 95 or 98%. In certain embodiments, it is contemplated that ibrutinib is formulated having the R enantiomer with less than 10, 5, or 3% by weight of other impurities such as the S enantiomer and/or other synthetic byproducts.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxyl group. The derivative may be a prodrug. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or an amine functional group in the active compound and the like.

Bruton's tyrosine kinase (BTK) catalyzes the phosphorylation phospholipase-Cγ (PLCγ) which is involved in the survival of leukemic cells in various B cell malignancies. BTK inhibitors typically specifically bind to the active phosphorylation site leading to inhibition of B cell development. Honigberg et al. Proc Natl Acad Sci USA, 2010, 107(29): 13075-13080. BTK is mutated in the primary immunodeficiency X-linked agammaglobulinemia (XLA) as reported in Vetrie et al. Nature, 1993, 361:226-33.

Ibrutinib and derivatives thereof are reported in WO2008039218. In certain embodiments, ibrutinib or derivative is a compound having the following formula:

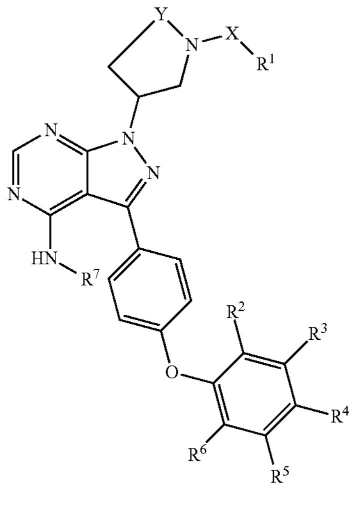

or salt thereof, wherein,

X is C═O, or $SO_2$.

Y is —$CH_2CH_2$— or —$CH_2$—;

$R^1$ is alkenyl or alkynyl;

$R^2$, $R^3$, $R^4$, $R^5$, or $R^6$ are each, individually and independently, hydrogen, halogen alkoxy, or alkyl; and $R^7$ is hydrogen or alkyl.

In certain embodiments, ibrutinib or a derivative is a compound selected from 1-(3-(4-amino-3-(4-phenoxyphenyl)-1H-pyrazolo[3,4-d]pyrimidin-1-yl)piperidin-1-yl)prop-2-en-1-one; (E)-1-(3-(4-amino-3-(4-phenoxyphenyl)-1H-pyrazolo[3,4-d]pyrimidin-1-yl)piperidin-1-yl)but-2-en-1-one; 1-(3-(4-amino-3-(4-phenoxyphenyl)-1H-pyrazolo[3,4-d]pyrimidin-1-yl)piperidin-1-yl)sulfonylethene; 1-(3-(4-amino-3-(4-phenoxyphenyl)-1H-pyrazolo[3,4-d]pyrimidin-1-yl)piperidin-1-yl)prop-2-yn-1-one; 1-((R)-3-(4-amino-3-(4-phenoxyphenyl)-1H-pyrazolo[3,4-d]pyrimidin-1-yl)pyrrolidin-1-yl)prop-2-en-1-one; and N-(1-(1-acryloylpiperidin-3-yl)-3-(4-phenoxyphenyl)-1H-pyrazolo[3,4-d]pyrimidin-4-yl)acetamide or salt thereof.

Ibrutinib or derivative may be administered orally via the gastrointestinal tract or by injection, at clinical doses of about 50 mg/day to 1000 mg/day, 100 mg/day to 1000 mg/day, 200 mg/day to 1000 mg/day, 400 mg/day to 1000 mg/day, 50 mg/day to 500 mg/day, 100 mg/day to 500 mg/day, 200 mg/day to 500 mg/day, 400 mg/day to 500 mg/day, 50 mg/day to 300 mg/day, 100 mg/day to 300 mg/day, 200 mg/day to 300 mg/day, 20 mg/day to 200 mg/day, or 20 mg/day to 300 mg/day. The side effects associated with the use of ibrutinib at high doses (e.g., 420 mg/day or 840 mg/day) are reported to include nausea or emesis, dizziness, and diarrhea.

Methods of Use

This disclosure relates to using compounds disclosed herein to treat or prevent cocaine use disorder, cocaine toxicity, or other drug related disorders. In certain embodiments, this disclosure relates to methods of treating a drug addiction or to help prevent relapse. In certain embodiments, this disclosure relates to methods of treating or preventing cocaine use disorder, cocaine toxicity, or other use disorders comprising administering an effective amount of a compound disclosed herein, such as ibrutinib, [(R)-1-(3-(4-amino-3-(4-phenoxyphenyl)-1H-pyrazolo[3,4-d]pyrimidin-1-yl)piperidin-1-yl)prop-2-en-1-one], derivative, or salt thereof to a subject in need thereof. In certain embodiments, the compound is a Bruton's tyrosine kinase (BTK) inhibitor.

In certain embodiments, the subject has admitted having or is diagnosed with an addiction to cocaine, methamphetamine, alcohol, tobacco, opioids, or other addictive drug, or diagnosed with, at risk of, or exhibiting symptoms of such a drug addiction. In certain embodiments, the subject is a human patient. In certain embodiments, the subject has accepted the terms of an inpatient or outpatient drug rehabilitation treatment plan.

In certain embodiments, this disclosure relates to methods of treating cocaine use disorder comprising administering an effective amount of compound disclosed herein, a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof, to a subject in need thereof.

In certain embodiments, the subject has admitted or is diagnosed with having an addiction to cocaine use. In certain embodiments, a Bruton's tyrosine kinase (BTK) inhibitor such as ibrutinib is administered in combination with cocaine. In certain embodiments, the subject has ceased to ingest cocaine for more than 2 days. In certain embodiments, the subject has ceased to ingest cocaine for more than 7 days. In certain embodiments, the subject is human.

In certain embodiments, the subject has ceased to ingest cocaine for more than 2 days. In certain embodiments, the subject has ceased to ingest cocaine for more than 7 days. In certain embodiments, a Bruton's tyrosine kinase (BTK) inhibitor such as ibrutinib is administered in combination with methadone, buprenorphine, or naltrexone. In certain embodiments, the subject is a human patient. In certain embodiments, the subject has accepted the terms of a drug rehabilitation center treatment plan.

In certain embodiments, this disclosure relates to methods of treating or preventing a relapse of cocaine use comprising administering an effective amount of compound disclosed herein a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

In certain embodiments, the subject has ceased to ingest cocaine for more than 2 days. In certain embodiments, the subject has ceased to ingest cocaine for more than 7 days. In certain embodiments, a Bruton's tyrosine kinase (BTK) inhibitor such as ibrutinib is administered in combination with methadone, buprenorphine, or naltrexone. In certain embodiments, the subject is a human patient.

In certain embodiments, this disclosure relates to methods of treating or preventing cocaine neurotoxicity comprising administering an effective amount of compound disclosed herein or a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

In certain embodiments, a Bruton's tyrosine kinase (BTK) inhibitor such as ibrutinib is administered in combination with a benzodiazepine. In certain embodiments, the benzodiazepine is diazepam, clonazepam, or midazolam. In certain embodiments, ibrutinib is administered in combination with an antipsychotic medication. In certain embodiments, the antipsychotic medication is ziprasidone, haloperidol, chlorpromazine, or olanzapine.

In certain embodiments, this disclosure relates to methods of treating or preventing cocaine-induced seizures comprising administering an effective amount of compound disclosed herein or a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

In certain embodiments, a Bruton's tyrosine kinase (BTK) inhibitor such as ibrutinib is administered in combination with a benzodiazepine. In certain embodiments, the benzodiazepine is diazepam, clonazepam, or midazolam. In certain embodiments, ibrutinib is administered in combination with an antipsychotic medication. In certain embodiments, the antipsychotic medication is ziprasidone, haloperidol, chlorpromazine, or olanzapine.

In certain embodiments, this disclosure relates to methods of treating or preventing cocaine induced cardiovascular effects comprising administering an effective amount of compound disclosed herein or a Bruton's tyrosine kinase (BTK) inhibitor such as (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

In certain embodiments, a Bruton's tyrosine kinase (BTK) inhibitor such as ibrutinib is administered in combination with vasopressin or epinephrine.

In certain embodiments a compound, e.g., a Bruton's tyrosine kinase (BTK) inhibitor such as ibrutinib or derivative thereof as disclosed herein, is administered in an amount sufficient to treat a drug-related disorder, e.g., cocaine-related disorder. The treatment as used herein encompasses a reduction in clinical symptoms or side effects of the cocaine use or reduction in the frequency of cocaine use, or elimination of cocaine use, e.g., for a time of greater than one, two, three, four, five, or six months, or more than one or two years. Signs of cocaine use include dilated pupils, long periods of wakefulness, loss of appetite, over-excitement, paranoia, runny nose or frequent sniffles, high blood pressure, and/or damage to the nasal cavity and septum. Adverse side effects of cocaine use include headaches, high blood pressure, nausea, trouble sleeping, coma, chills, confusion, sweating, and seizures.

In certain embodiments, this disclosure contemplates using a Bruton's tyrosine kinase (BTK) inhibitor such as ibrutinib or derivatives for uses in treating cocaine use disorders done in addition to providing counseling at psychotherapy sessions, e.g., providing instruction on cognitive behavioral strategies and/or for contingency management. Contingency management typically involves providing the subject with incentives or rewards for meeting specific behavioral goals (e.g., verified abstinence), e.g., allowing a patient the privilege of self-administration of methadone doses contingent on providing cocaine-free urine specimens. Cognitive behavior strategies typically try to prevent relapse by providing instructions so that the subject learns to recognize situations or states which lead to drug use, so as to avoid or cope with these high-risk situations.

Pharmaceutical Compositions

In certain embodiments, this disclosure relates to pharmaceutical compositions comprising a compound disclosed herein, a Bruton's tyrosine kinase (BTK) inhibitor such as ibrutinib, and a pharmaceutically acceptable excipient. In certain embodiments, the pharmaceutical composition comprises the compound, a Bruton's tyrosine kinase (BTK) inhibitor such as as ibrutinib, and another active ingredient. In certain embodiments, the active ingredient is methadone, buprenorphine, or naltrexone. In certain embodiments, the active ingredient is a benzodiazepine such as diazepam, clonazepam, or midazolam. In certain embodiments, the active ingredient is an antipsychotic medication such as ziprasidone, haloperidol, chlorpromazine, or olanzapine. In certain embodiments, the active ingredient is vasopressin or epinephrine.

In certain embodiments, the pharmaceutical composition in the form of a table, pill, capsule, or gel. In certain embodiments, the pharmaceutical composition in the form or a liquid comprising pH buffering agents and optionally salts and/or saccharide or polysaccharide.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

In certain embodiments, the pharmaceutical composition is in the form of a tablet, pill, capsule, powders, granules, gel, gel capsule, or cream. In such solid dosage forms, the active compound is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia gum, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof.

In certain embodiments, this disclosure contemplates an intravenous formulation with pH buffering agents and tonicity in a range representing physiological values (pH 7 to 8) or for bolus administration, e.g., containing normal saline or dextrose optionally containing pH buffering agents. In certain embodiments, the pharmaceutical composition is in the form of a sterilized pH buffered aqueous salt solution or a saline phosphate buffer between a pH of 6 to 8, optionally comprising a saccharide or polysaccharide.

In certain embodiments, a compound, e.g., a Bruton's tyrosine kinase (BTK) inhibitor such as ibrutinib, derivatives, or salts thereof as disclosed herein, may be administered by any suitable route or device. In one embodiment, a compound can be administered orally or by injection, e.g., an intravenous injection. In certain embodiments, it is contemplated a Bruton's tyrosine kinase (BTK) inhibitor such as ibrutinib and/or a pharmaceutically acceptable salt thereof is released in the small intestine. In certain embodiments, a Bruton's tyrosine kinase (BTK) inhibitor such as ibrutinib may be administered intraduodenally. In another embodiment, a Bruton's tyrosine kinase (BTK) inhibitor such as ibrutinib and/or a pharmaceutically acceptable salt thereof is released to a region of the intestine in which the pH is about 5, or 5, or greater than 5. In another embodiment, said a Bruton's tyrosine kinase (BTK) inhibitor such as ibrutinib and/or a pharmaceutically acceptable salt thereof is released to a region of the intestine in which the pH is about 5.5, or greater than about pH 5.5. For example, the release is in one or more of the duodenum, jejunum, ileum, and colon. In one embodiment, the release is in one or more of the duodenum, jejunum, or ileum.

In one embodiment, the release to the above regions of the intestine is achieved by coating a Bruton's tyrosine kinase (BTK) inhibitor such as ibrutinib and/or a pharmaceutically acceptable salt thereof or the dosage form containing ibrutinib and/or a pharmaceutically acceptable salt thereof with at least one coating chosen from enteric coatings and non-enteric time-delayed release coatings. In one embodiment, the release to the above regions of the intestine is achieved by coating ibrutinib and/or a pharmaceutically acceptable salt thereof or the dosage form containing a Bruton's tyrosine kinase (BTK) inhibitor such as ibrutinib and/or a pharmaceutically acceptable salt thereof with at least one coating chosen from enteric coatings. In one embodiment, the release to the above regions of the intestine is achieved by coating a Bruton's tyrosine kinase (BTK) inhibitor such as ibrutinib and/or a pharmaceutically acceptable salt thereof or the dosage form containing a Bruton's tyrosine kinase (BTK) inhibitor such as ibrutinib and/or a pharmaceutically acceptable salt thereof with at least one coating chosen from enteric coatings wherein the enteric coatings are chosen from polymeric coatings.

In another embodiment, the enteric coating is an anionic polymer such as polymethacrylates (e.g., poly methyl methacrylate, poly ethyl methacrylate, poly methacrylic acid); cellulose-based polymers (e.g., cellulose acetate phthalate (CAP), cellulose acetate trimellitate (CAT), cellulose acetate succinate (CAS), hydroxypropyl methylcellulose phthalate (HPMCP), and hydroxypropyl methylcellulose acetate succinate (HPMCAS)) or polyvinyl derivatives such as polyvinyl acetate phthalate (PVAP). When a non-enteric coating is employed, the time-delayed release dosage forms are administered in fasted state and the time-delayed release coating is designed to erode, burst, or become highly permeable in about 0.3 to about 3 hours or in about 0.5 to about 2 hours after administration to release ibrutinib and/or a pharmaceutically acceptable salt thereof.

Neuronal mRNA Mediated Drug Discovery for Cocaine Use Disorder (CUD) Using Human Brain Data The molecular neuropathology of CUD is characterized by persistent cellular and molecular adaptations across multiple brain regions, particularly in the meso-cortico-limbic "reward" pathway. Molecular neuro-adaptations in this pathway mediate reward, motivation, behavioral control, memory formation, incentive salience, cue, drug and stress-induced drug taking/relapse and ultimately compulsive drug use. One approach to investigate the neuro-molecular features underlying CUD is to examine gene expression profiles in post-mortem brain tissue by comparing individuals with CUD to matched cocaine-free controls. Three of such studies are publicly available and assess CUD gene expression profiles in key brain regions such as: the dorsal-lateral pre-frontal cortex, hippocampus, and midbrain. Importantly, medications that consistently target gene expression across meso-cortico-limbic brain regions have demonstrated robust effects for reducing binge drinking in mice. By searching for medications that target transcriptional patterns across relevant brain regions, medication can be identified that have promise for treating CUD.

Analyses were performed on human samples (n=71) of publicly available gene expression data from brain tissue (post-mortem) of individuals with cocaine use disorder (CUD; n=36) and matched cocaine-free controls (n=35) from three independent studies. Drug discovery analyses was conducted by leveraging the L1000 database, which catalogues mRNA expression profiles of human cell types exposed to therapeutic compounds. Three categories were used as input for drug discovery analysis. The first category included the differentially expressed genes (FDR<0.05) associated with CUD in the dlPFC, hippocampus, and midbrain. Differentially expressed genes might include genes attributed to cocaine-induced toxicity, cardiac complications or other sources of biases (e.g., psychiatric co-morbidity). To focus on the genes related to the behavioral manifestations of CUD, the mRNA expression of genes from the cocaine addiction pathway were investigated (Kyoto Encyclopedia of Genes and Genomes [KEGG]database). To further minimize potential biases of measurement error by employing "landmark" genes (those directly measured from L1000, rather than imputed), those that were part of at least one of the first two categories were sought.

Drug-discovery analyses utilized the L1000 Connectivity Mapping gene expression profiles from the Library of Integrated Network Based Cellular Signatures (level 5 data from phase I: GSE92742 and phase II: GSE70138). Since the focus of the study was to find repurposable treatments for CUD, all compounds that were FDA approved or in stage 1-3 of clinical trials were selected—as listed from the drug repurposing hub website. Findings were benchmarked with treatments that were currently undergoing clinical trials for CUD. The mechanisms of action for most pharmacological treatments of substance use disorders target neuronal processes. Thus, the drug discovery analysis was focused on the two neuronal cell types used in the L1000 database: regular neuronal cells and neuronal progenitor cells. In total, the potential therapeutic value of 835 compounds were evaluated, which spanned 3,468 individual neuronal mRNA signatures (measured in vitro gene expression profiles for a compound at a particular dose, time, and cell type). For each signature a linear Pearson Product-Moment correlation coefficient with the CUD input was assessed and the standard error was derived. Note that not all medications undergoing clinical trials for CUD were included in the human neuronal cell lines from the L1000 database.

To identify potential treatments for CUD, multi-level meta regressions were conducted for all 835 compounds using the meta for package in R. Meta-regressions were adjusted for two random effects: human brain region (or study) and the three input categories within studies. Each compound was treated as a fixed effect incorporating the effect size (r) and sampling variability (se2r) for neuronal signatures of a compound. Theoretically, if the transcriptional signature of a compound is negatively associated with a diseased state, this compound may 'reverse' the underlying disease mechanisms back to 'normal' and thus may increase the likelihood of demonstrating clinical utility. Hence compounds with negative meta-regression coefficients that also survived correction for multiple testing (BH-FDR adjusted p-value <0.05) were emphasized as potential treatments.

The potential treatments were indirectly validated and identified from drug discovery analysis using two independent transcriptome-wide datasets. These datasets included a human neuronal (SH-SY5Y neuroblastoma cells) cocaine exposure model (GSE71939) and a mouse model of cocaine self-administration (GSE110344). The neuronal cocaine exposure dataset included 18 samples that assessed RNA expression (via microarray) for two time points (6 or 24 hours post exposure) across three doses (0 uM, 1 uM and 5 uM; the latter two mimic biologically relevant cocaine levels found in individuals with cocaine abuse). The mouse validation RNA-seq data was collected from 12-15 male C576LBJ mice using similar brain regions to the human samples (VTA, hippocampus and PFC). Mice either pressed a lever to receive intravenous infusions of cocaine (1 mg/kg; 2 hour sessions for 2 weeks) or saline. Brain tissue was extracted 24 hours after the last self-administration session. Note that the mouse validation was limited to orthologous genes listed from the mouse genome informatics dataset. To maintain consistency, the data processing and analysis was harmonized for validation datasets to resemble the human brain data. Using multi-level meta-regression, experiments were performed to determine whether the potential CUD treatments were also negatively associated with the differential expression of the CUD genes within the validation datasets—accounting for dose and time (neuronal exposure data) or brain region (mouse data) as random effects. A significant association from this (indirect) validation analysis was interpreted as evidence that a potential treatment interferes with the neurochemical and/or behavioral manifestations of cocaine use.

Results

The input of drug discovery analysis was investigated. Minimal overlap was observed among the DEGs identified across human brain regions. Associations among KEGG cocaine addiction genes were modest and sometimes negative. This heterogeneity may reflect the difficulty of identifying an effective treatment that accommodates multiple brain regions (and individuals).

Figure 1A:
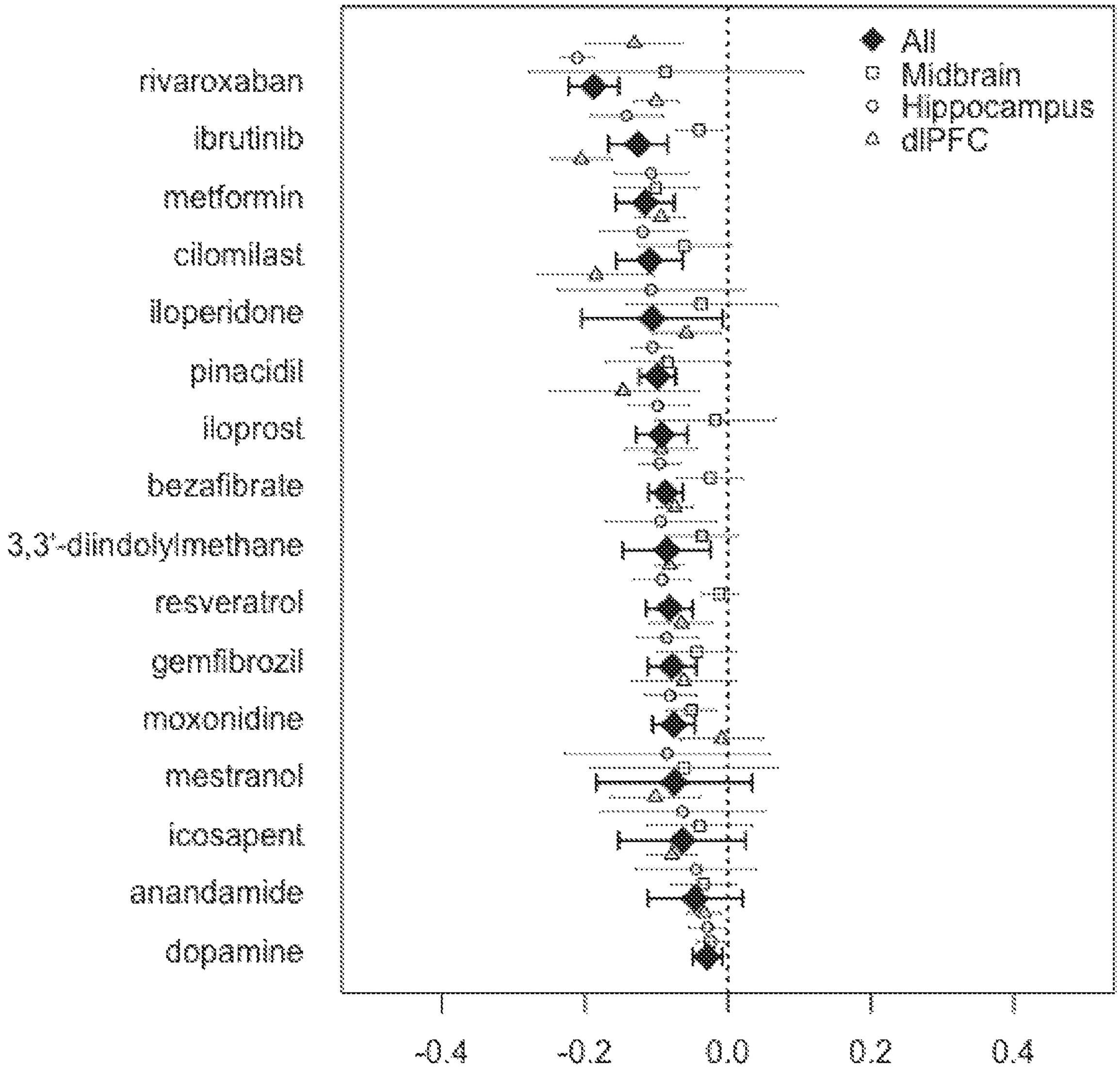
FIG. 1A shows calculated cocaine associations (mean weighted r) using mRNA profiles from brain tissues indicating potential treatments for CUD.
Figure 1B:
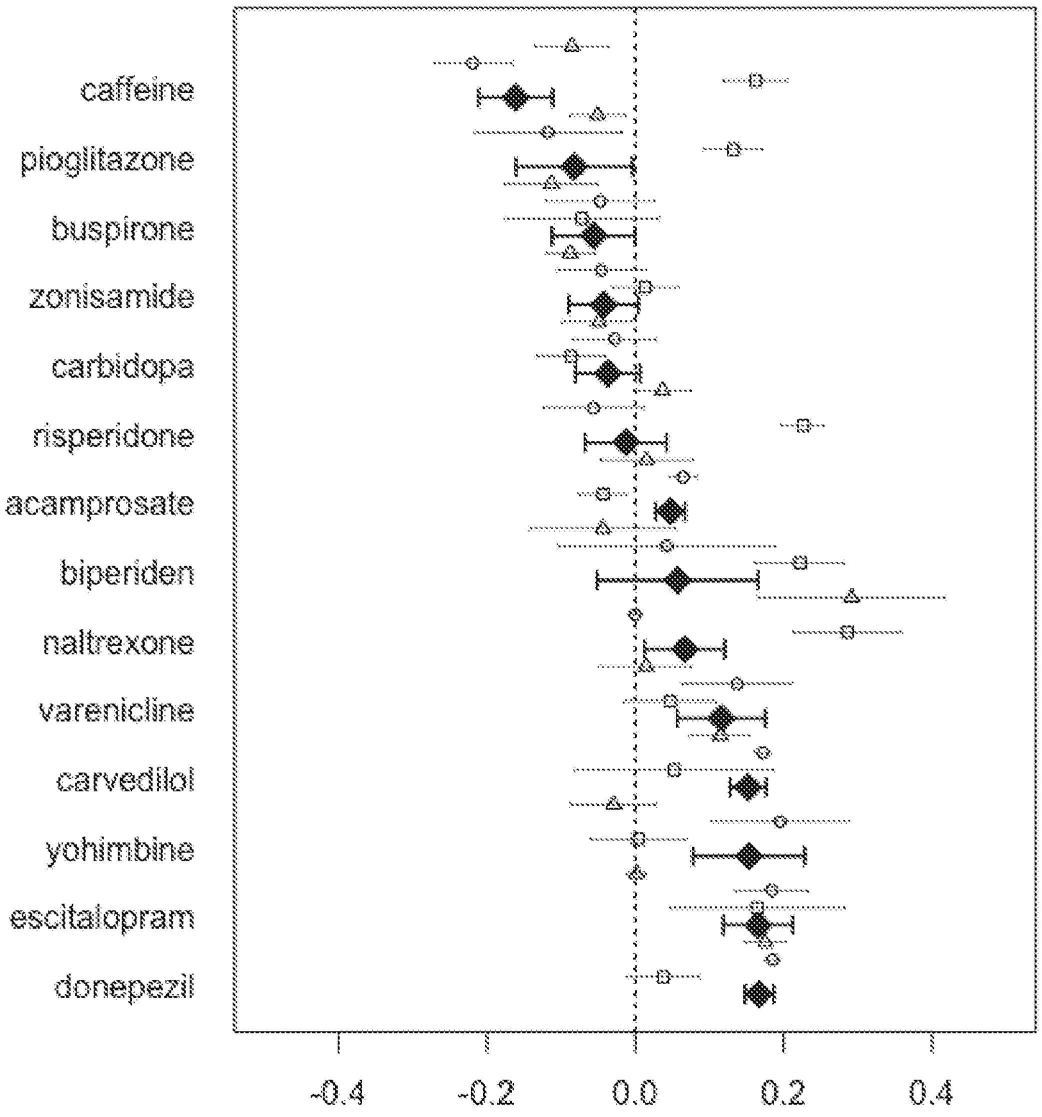
FIG. 1B shows calculated cocaine associations (mean weighted r) using mRNA profiles from brain tissues for drugs that were in clinical trials for CUD treatment.

Sixteen potential treatments were identified that may reverse the neuropathology of CUD in the midbrain, hippocampus and dlPFC ($padj<0.05$; see FIG. 1A), which had diverse pharmacological mechanisms of action. These potential treatments outperformed the current pharmaceuticals undergoing clinical trials for CUD (see FIG. 1). Of note, the clinical trial treatments seemed to have more heterogeneity across brain regions than the potential treatments identified in the analyses.

Figure 2:
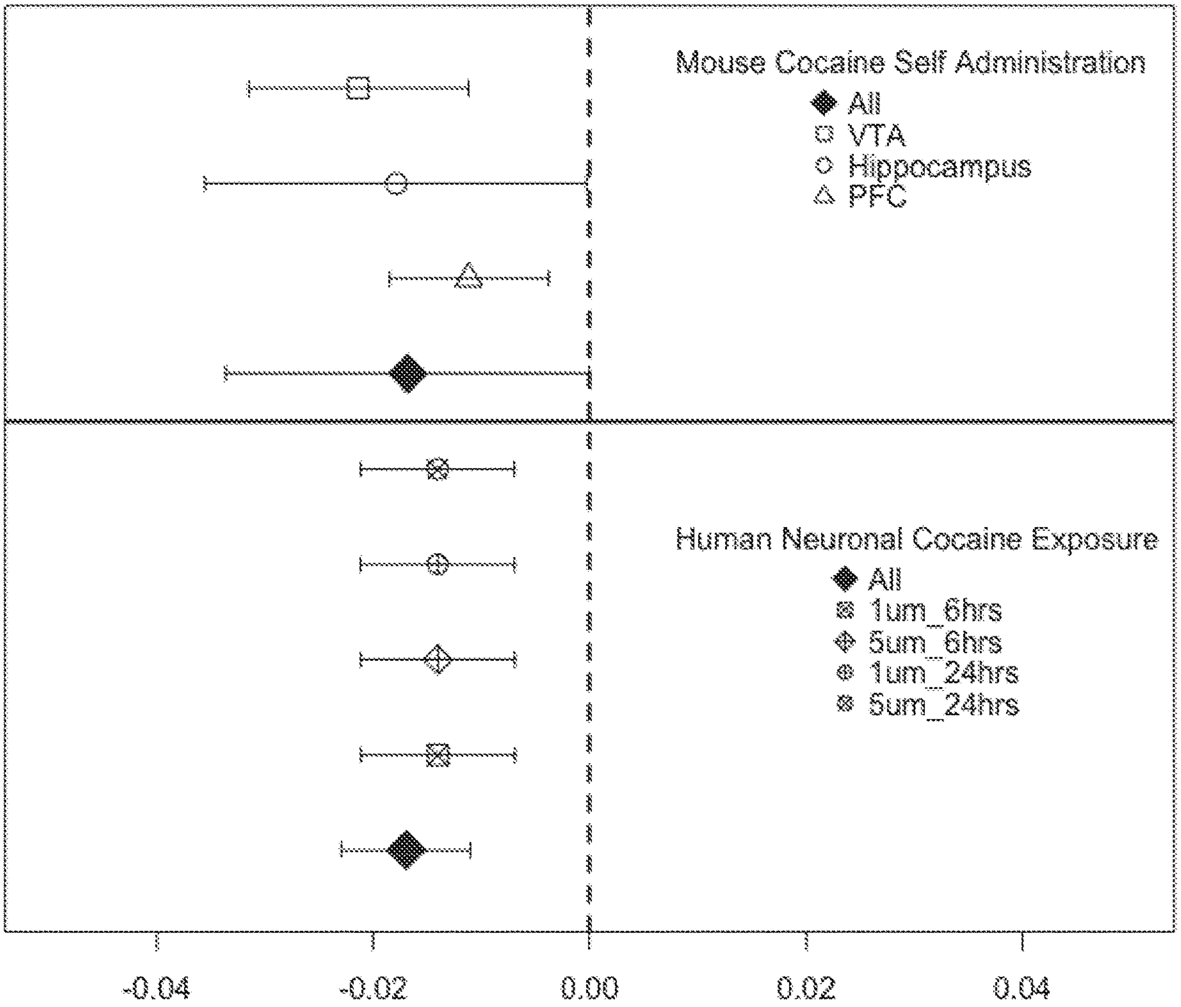
FIG. 2 shows validation data for cocaine association (mean weighted r) of ibrutinib indicating utility for treating CUD.

The validity of the 16 potential treatments were tested using independent in vitro and in vivo datasets. Ibrutinib, significantly reversed the CUD genes in human neuronal cells exposed to cocaine ($p=0.001$; $padj=0.019$) and trended to counteract the epigenetic profiles associated with mouse cocaine self-administration ($p=0.007$; $padj=0.0732$; see FIG. 2).

Validation of Potential Therapeutic Efficacy of Ibrutinib in the *Drosophila* Model The initial data indicated ibrutinib may have negative associations with both neuronal cocaine exposure and mouse cocaine self-administration. To obtain experimental confirmation of therapeutic effects of ibrutinib on CUD, a *Drosophila melanogaster* model was used. This model enables high throughput quantification of behavioral responses in defined genetic backgrounds and controlled environmental conditions. Ibrutinib altered cocaine-induced changes in startle response and reduced the occurrence of cocaine-induced seizures (n=61-142 per group; sex: 51% female), indicating ibrutinib is useful as a potential therapeutic for cocaine neurotoxicity.

*Drosophila* provides an advantageous model system for studies on cocaine consumption. The *Drosophila* dopamine transporter contains a binding site that can accommodate cocaine, and exposure to cocaine gives rise to motor responses that resemble behaviors observed in rodents. In addition, flies develop sensitization to repeated intermittent exposure to cocaine. Startle behavior and the prevalence of seizure activity was measured in male and female flies. Measurements were taken following acute consumption of solid food, solid food supplemented with cocaine, or solid food supplemented with cocaine and ibrutinib. Male flies exposed to cocaine spent less time moving after being subjected to a mechanical startle (FIG. 3A). This is likely due to the occurrence of cocaine-induced seizures, which were scored as stationary periods. Both male and female flies that consumed ibrutinib with cocaine spent more time moving than flies that only consumed cocaine (FIG. 3A). Male flies that consumed ibrutinib and cocaine showed a significant decrease in the prevalence of seizures (FIG. 3B). Fewer cocaine-induced seizures were also observed in ibrutinib treated females, but this observation did not reach statistical significance since the incidence of cocaine-induced seizures was lower in females than in males. These results confirm that ibrutinib may be useful as a therapeutic to prevent various neurobehavioral and neurotoxic effects of cocaine use.

This data suggests that ibrutinib may target and reverse the expression of cocaine addiction genes in human meso-cortico-limbic circuitry. Notably, ibrutinib shares a pharmacological mechanism of action with terreic acid, Bruton's tyrosine kinase (BTK) inhibitors, a compound that reduced binge drinking in mice. Thus, it is contemplated that terreic acid can used for any of the embodiments disclosed herein. It is also contemplated that other Bruton's tyrosine kinase (BTK) inhibitors such as pirtobrutinib, acalabrutinib, and zanubrutinib, can used in any of the embodiments disclosed herein. Ibrutinib influences intracellular cascades involved in pro-inflammatory response, Ca+ signaling and protein kinase activity. These processes are also involved in cocaine use, and cocaine induced seizures.

In addition to ibrutinib, other potential medications are identified that may counter some of the neuroadaptations of CUD. Some of these compounds may target molecular processes underlying chronic cocaine use. For instance, dopamine reversed the differential expression of CUD genes across brain regions, which may counteract the hypodopaminergic state induced by chronic cocaine use. It is contemplated that dopamine can used in any of the embodiments disclosed herein.

A preponderance of the drugs tested seemed to be sensitive to various cardiac complications associated with cocaine use, such as rivaroxaban, pinacidil, iloprost, gemfibrozil, bezafibrate and moxonidine. It is possible that these medications exert a neuroprotective role for cocaine use and may be relevant for cocaine toxicity. Thus, it is contemplated that rivaroxaban, pinacidil, iloprost, gemfibrozil, bezafibrate and moxonidine can used in any of the embodiments disclosed herein.

The invention claimed is:

1. A method of treating cocaine use disorder comprising administering an effective amount of (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof, to a subject in need thereof.

2. The method of claim 1, wherein ibrutinib is administered in combination with cocaine.

3. The method of claim 1, wherein the subject is human.

4. A method of preventing a relapse of cocaine use comprising administering an effective amount of (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

5. The method of claim 4, wherein ibrutinib is administered in combination with methadone, buprenorphine, or naltrexone.

6. The method of claim 4, wherein the subject is a human patient.

7. The method of claim 4, wherein the subject has accepted the terms of a drug rehabilitation center treatment plan.

8. A method of treating or preventing cocaine neurotoxicity comprising administering an effective amount of (R)-1-(3-(4-amino-3-(4-phenoxyphenyl)-1H-pyrazolo[3,4-d]pyrimidin-1-yl)piperidin-1-yl)prop-2-en-1-one (ibrutinib) or salt thereof to a subject in need thereof.

9. The method of claim 8, wherein ibrutinib is administered in combination with a benzodiazepine.

10. The method of claim 9, wherein the benzodiazepine is diazepam, clonazepam, or midazolam.

11. The method of claim 8 wherein ibrutinib is administered in combination with an antipsychotic medication.

12. The method of claim 11, wherein the antipsychotic medication is ziprasidone, haloperidol, chlorpromazine, or olanzapine.

13. The method of claim 8 wherein the method of treating or preventing cocaine neurotoxicity is treating or preventing cocaine-induced seizures comprising administering an effective amount of (R)-1-(3-(4-amino-3-(4-phenoxyphenyl)-1H-pyrazolo[3,4-d]pyrimidin-1-yl)piperidin-1-yl) prop-2-en-1-one (ibrutinib) or salt thereof to a subject in need thereof.

* * * * *